United States Patent
Bollinger et al.

(10) Patent No.: US 8,266,780 B2
(45) Date of Patent: Sep. 18, 2012

(54) METHOD AND APPARATUS FOR USE OF POROUS IMPLANTS

(75) Inventors: Mark A. Bollinger, Fort Wayne, IN (US); Brian M. May, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 484 days.

(21) Appl. No.: 12/038,570

(22) Filed: Feb. 27, 2008

(65) Prior Publication Data

US 2008/0147187 A1    Jun. 19, 2008

Related U.S. Application Data

(63) Continuation-in-part of application No. 11/294,692, filed on Dec. 5, 2005, which is a continuation-in-part of application No. 11/111,123, filed on Apr. 21, 2005, now abandoned.

(51) Int. Cl.
*B23P 11/02* (2006.01)

(52) U.S. Cl. ................ 29/447; 623/23.3; 623/23.55

(58) Field of Classification Search ............. 29/447, 29/405, 507; 403/273; 623/23.3, 23.55; 428/613; 228/229, 230
See application file for complete search history.

(56) References Cited

U.S. PATENT DOCUMENTS

| | | | |
|---|---|---|---|
| 3,353,259 A | 11/1967 | Kirkpatrick | |
| 3,579,805 A * | 5/1971 | Kast | 148/529 |
| 3,605,123 A | 9/1971 | Hahn | |
| 3,677,795 A | 7/1972 | Bokros et al. | |
| 3,808,606 A | 5/1974 | Tronzo | |
| 3,840,904 A | 10/1974 | Tronzo | |
| 3,855,638 A | 12/1974 | Pilliar et al. | |
| 3,896,500 A | 7/1975 | Rambert et al. | |
| 3,905,777 A | 9/1975 | Lacroix et al. | |
| 3,906,550 A | 9/1975 | Rostoker et al. | |
| 3,938,499 A | 2/1976 | Bucalo | |
| 3,986,212 A | 10/1976 | Sauer | |
| 4,051,559 A | 10/1977 | Pifferi et al. | |
| 4,164,794 A | 8/1979 | Spector et al. | |
| 4,168,326 A | 9/1979 | Broemer et al. | |
| 4,184,213 A | 1/1980 | Heimke et al. | |
| 4,187,559 A | 2/1980 | Grell et al. | |
| 4,205,400 A | 6/1980 | Shen et al. | |

(Continued)

FOREIGN PATENT DOCUMENTS

DE    2404214    8/1974

(Continued)

OTHER PUBLICATIONS

"Magnum™ large metal articulation, Surgical Technique" brochure, Biomet Orthopedics, Inc., 2004 (12 pages).

(Continued)

*Primary Examiner* — David Bryant
*Assistant Examiner* — Jacob Cigna
(74) *Attorney, Agent, or Firm* — Harness, Dickey (57) ABSTRACT

An orthopedic implant. The implant includes a metal portion having an internal three-dimensional cavity, the cavity having an opening to an outer surface of the metal portion, a ledge circumferentially surrounding at least a portion of the opening, and a porous metal insert formed in a three-dimensional shape conforming to the shape of the cavity and enclosed by the cavity without being bonded to the cavity. The insert is retained inside the cavity by the ledge.

30 Claims, 2 Drawing Sheets

U.S. PATENT DOCUMENTS

| | | |
|---|---|---|
| 4,206,271 A | 6/1980 | Norling et al. |
| 4,217,666 A | 8/1980 | Averill |
| 4,224,698 A | 9/1980 | Hopson |
| 4,234,972 A | 11/1980 | Hench et al. |
| 4,285,070 A | 8/1981 | Averill |
| 4,285,071 A | 8/1981 | Nelson et al. |
| 4,307,472 A | 12/1981 | Morris |
| 4,309,488 A | 1/1982 | Heide et al. |
| 4,330,891 A | 5/1982 | Branemark et al. |
| 4,345,339 A | 8/1982 | Muller et al. |
| 4,351,069 A | 9/1982 | Ballintyn et al. |
| 4,355,428 A | 10/1982 | Deloison et al. |
| 4,362,681 A | 12/1982 | Spector et al. |
| 4,479,271 A | 10/1984 | Bolesky et al. |
| 4,542,539 A | 9/1985 | Rowe, Jr. et al. |
| 4,563,778 A | 1/1986 | Roche et al. |
| 4,566,138 A | 1/1986 | Lewis et al. |
| 4,570,271 A | 2/1986 | Sump |
| 4,612,160 A | 9/1986 | Donlevy et al. |
| 4,636,219 A | 1/1987 | Pratt et al. |
| 4,644,942 A | 2/1987 | Sump |
| 4,659,331 A | 4/1987 | Matthews et al. |
| 4,666,450 A | 5/1987 | Kenna |
| 4,685,923 A | 8/1987 | Mathys et al. |
| 4,693,721 A | 9/1987 | Ducheyne |
| 4,715,859 A | 12/1987 | Schelhas et al. |
| 4,715,860 A | 12/1987 | Amstutz et al. |
| 4,743,256 A | 5/1988 | Brantigan |
| 4,743,262 A | 5/1988 | Tronzo |
| 4,750,905 A * | 6/1988 | Koeneman et al. ........ 623/23.51 |
| 4,756,862 A | 7/1988 | Spector et al. |
| 4,769,041 A | 9/1988 | Morscher et al. |
| 4,778,473 A | 10/1988 | Matthews et al. |
| 4,778,474 A | 10/1988 | Homsy |
| 4,795,469 A | 1/1989 | Oh |
| 4,801,301 A | 1/1989 | Noiles |
| 4,813,959 A | 3/1989 | Cremascoli et al. |
| 4,828,565 A | 5/1989 | Duthoit et al. |
| 4,840,632 A | 6/1989 | Kampner |
| 4,842,606 A | 6/1989 | Kranz et al. |
| 4,851,006 A | 7/1989 | Tuke et al. |
| 4,854,496 A | 8/1989 | Bugle |
| 4,863,474 A | 9/1989 | Brown et al. |
| 4,863,475 A | 9/1989 | Andersen et al. |
| 4,863,538 A | 9/1989 | Deckard |
| 4,871,368 A | 10/1989 | Wagner et al. |
| 4,883,490 A | 11/1989 | Oh |
| 4,883,491 A | 11/1989 | Mallory et al. |
| 4,892,549 A | 1/1990 | Figgie, III et al. |
| 4,904,265 A | 2/1990 | MacCollum et al. |
| 4,919,666 A * | 4/1990 | Buchhorn et al. ......... 623/16.11 |
| 4,919,675 A | 4/1990 | Dietschi et al. |
| 4,923,473 A | 5/1990 | Griss et al. |
| 4,936,847 A | 6/1990 | Manginelli |
| 4,936,856 A | 6/1990 | Keller et al. |
| 4,936,861 A | 6/1990 | Muller et al. |
| 4,944,759 A | 7/1990 | Mallory et al. |
| 4,950,270 A | 8/1990 | Bowman et al. |
| 4,950,299 A | 8/1990 | Noiles |
| 4,955,919 A | 9/1990 | Pappas et al. |
| 4,957,819 A | 9/1990 | Kawahara et al. |
| 4,963,154 A | 10/1990 | Anapliotis et al. |
| 4,969,907 A | 11/1990 | Koch et al. |
| 4,969,910 A | 11/1990 | Frey et al. |
| 4,976,738 A | 12/1990 | Frey et al. |
| 4,978,355 A | 12/1990 | Frey et al. |
| 4,978,356 A | 12/1990 | Noiles |
| 4,978,358 A | 12/1990 | Bobyn |
| 4,997,445 A | 3/1991 | Hodorek |
| 5,004,476 A | 4/1991 | Cook |
| 5,009,665 A | 4/1991 | Serbousek et al. |
| 5,013,324 A | 5/1991 | Zolman et al. |
| 5,018,285 A | 5/1991 | Zolman et al. |
| 5,019,105 A | 5/1991 | Wiley |
| 5,021,062 A | 6/1991 | Adrey et al. |
| 5,021,063 A | 6/1991 | Tager et al. |
| 5,024,670 A | 6/1991 | Smith et al. |
| 5,027,998 A | 7/1991 | Bugle |
| 5,030,233 A | 7/1991 | Ducheyne |
| 5,047,182 A | 9/1991 | Sundback et al. |
| 5,080,672 A | 1/1992 | Bellis et al. |
| 5,080,674 A | 1/1992 | Jacobs et al. |
| 5,080,685 A | 1/1992 | Bolesky et al. |
| 5,084,051 A | 1/1992 | Tormala et al. |
| 5,092,897 A | 3/1992 | Forte |
| 5,096,518 A | 3/1992 | Fujikawa et al. |
| 5,098,435 A | 3/1992 | Stednitz et al. |
| 5,104,410 A | 4/1992 | Chowdhary |
| 5,108,432 A | 4/1992 | Gustavson |
| 5,120,175 A * | 6/1992 | Arbegast et al. ............. 411/501 |
| 5,133,764 A | 7/1992 | Pappas et al. |
| 5,152,796 A | 10/1992 | Slamin |
| 5,152,797 A | 10/1992 | Luckman et al. |
| 5,156,626 A | 10/1992 | Broderick et al. |
| 5,163,961 A | 11/1992 | Harwin |
| 5,167,502 A | 12/1992 | Kawahara et al. |
| 5,176,711 A | 1/1993 | Grimes |
| 5,181,928 A | 1/1993 | Bolesky et al. |
| 5,192,329 A | 3/1993 | Christie et al. |
| 5,198,308 A | 3/1993 | Shetty et al. |
| 5,201,766 A | 4/1993 | Georgette |
| 5,203,787 A | 4/1993 | Noblitt et al. |
| 5,211,665 A | 5/1993 | Ku et al. |
| 5,226,915 A | 7/1993 | Bertin |
| 5,236,457 A | 8/1993 | Devanathan |
| 5,236,462 A | 8/1993 | Mikhail |
| 5,246,530 A | 9/1993 | Bugle et al. |
| 5,282,861 A | 2/1994 | Kaplan |
| 5,286,260 A | 2/1994 | Bolesky et al. |
| 5,290,315 A | 3/1994 | DeCarlo, Jr. |
| 5,310,408 A | 5/1994 | Schryver et al. |
| 5,314,490 A | 5/1994 | Wagner et al. |
| 5,323,954 A | 6/1994 | Shetty et al. |
| 5,326,367 A | 7/1994 | Robioneck et al. |
| 5,326,368 A | 7/1994 | Collazo |
| 5,343,877 A | 9/1994 | Park |
| 5,348,788 A | 9/1994 | White |
| 5,358,532 A | 10/1994 | Evans et al. |
| 5,360,448 A | 11/1994 | Thramann |
| 5,360,452 A | 11/1994 | Engelhardt et al. |
| 5,370,692 A | 12/1994 | Fink et al. |
| 5,370,698 A | 12/1994 | Heimke et al. |
| 5,370,702 A | 12/1994 | Jones |
| 5,370,704 A | 12/1994 | DeCarlo, Jr. |
| 5,370,706 A | 12/1994 | Bolesky et al. |
| 5,376,122 A | 12/1994 | Pappas et al. |
| 5,380,325 A | 1/1995 | Lahille et al. |
| 5,397,359 A | 3/1995 | Mittelmeier et al. |
| 5,405,389 A | 4/1995 | Conta et al. |
| 5,415,704 A | 5/1995 | Davidson |
| 5,443,510 A | 8/1995 | Shetty et al. |
| 5,443,512 A | 8/1995 | Parr et al. |
| 5,443,519 A | 8/1995 | Averill et al. |
| 5,484,539 A | 1/1996 | Tersi et al. |
| 5,486,181 A | 1/1996 | Cohen et al. |
| 5,496,372 A | 3/1996 | Hamamoto et al. |
| 5,504,300 A | 4/1996 | Devanathan et al. |
| 5,505,984 A | 4/1996 | England et al. |
| 5,507,824 A | 4/1996 | Lennox |
| 5,509,933 A | 4/1996 | Davidson et al. |
| 5,534,027 A | 7/1996 | Hodorek |
| 5,535,810 A | 7/1996 | Compton et al. |
| 5,540,713 A | 7/1996 | Schnepp-Pesch et al. |
| 5,545,227 A | 8/1996 | Davidson et al. |
| 5,549,685 A | 8/1996 | Hayes |
| 5,549,691 A | 8/1996 | Harwin |
| 5,549,698 A | 8/1996 | Averill et al. |
| 5,549,701 A | 8/1996 | Mikhail |
| 5,571,187 A | 11/1996 | Devanathan |
| 5,571,194 A | 11/1996 | Gabriel |
| 5,571,198 A | 11/1996 | Drucker et al. |
| 5,571,200 A | 11/1996 | Cohen et al. |
| 5,571,201 A | 11/1996 | Averill et al. |
| 5,573,401 A | 11/1996 | Davidson et al. |
| 5,591,233 A * | 1/1997 | Kelman et al. ............. 623/23.51 |
| 5,593,451 A | 1/1997 | Averill et al. |
| 5,609,641 A | 3/1997 | Johnson et al. |

| Patent | Date | Name |
|---|---|---|
| 5,609,645 A | 3/1997 | Vinciguerra |
| 5,609,646 A | 3/1997 | Field et al. |
| 5,639,280 A | 6/1997 | Warner et al. |
| 5,658,338 A | 8/1997 | Tullos et al. |
| 5,658,347 A | 8/1997 | Sarkisian et al. |
| 5,658,348 A | 8/1997 | Rohr, Jr. |
| 5,665,119 A | 9/1997 | Koller et al. |
| 5,676,700 A | 10/1997 | Black et al. |
| 5,676,704 A | 10/1997 | Ries et al. |
| 5,688,453 A | 11/1997 | England et al. |
| 5,702,473 A | 12/1997 | Albrektsson et al. |
| 5,702,477 A | 12/1997 | Capello et al. |
| 5,702,483 A | 12/1997 | Kwong |
| 5,702,487 A | 12/1997 | Averill et al. |
| 5,723,011 A | 3/1998 | Devanathan et al. |
| 5,723,014 A | 3/1998 | Laurent et al. |
| 5,725,587 A | 3/1998 | Garber |
| 5,728,510 A | 3/1998 | White |
| 5,734,959 A | 3/1998 | Krebs et al. |
| 5,755,743 A | 5/1998 | Volz et al. |
| 5,755,806 A | 5/1998 | Stalcup et al. |
| 5,782,928 A | 7/1998 | Ries et al. |
| 5,782,929 A | 7/1998 | Sederholm |
| 5,798,308 A | 8/1998 | Chatterjee et al. |
| 5,824,107 A | 10/1998 | Tschirren et al. |
| 5,824,108 A | 10/1998 | Huebner |
| 5,863,295 A | 1/1999 | Averill et al. |
| 5,871,548 A | 2/1999 | Sanders et al. |
| 5,879,398 A | 3/1999 | Swarts et al. |
| 5,879,399 A | 3/1999 | Church et al. |
| 5,879,401 A | 3/1999 | Besemer et al. |
| 5,879,404 A | 3/1999 | Bateman et al. |
| 5,879,405 A | 3/1999 | Ries et al. |
| 5,888,205 A | 3/1999 | Pratt et al. |
| 5,904,720 A | 5/1999 | Farrar et al. |
| 5,916,268 A | 6/1999 | Schollner et al. |
| 5,925,077 A | 7/1999 | Williamson et al. |
| 5,926,685 A | 7/1999 | Krebs et al. |
| 5,931,870 A | 8/1999 | Cuckler et al. |
| 5,938,702 A | 8/1999 | Lopez et al. |
| 5,972,032 A | 10/1999 | Lopez et al. |
| 5,976,148 A | 11/1999 | Charpenet et al. |
| 5,981,828 A | 11/1999 | Nelson et al. |
| 5,989,293 A | 11/1999 | Cook et al. |
| 6,008,432 A | 12/1999 | Taylor |
| 6,013,104 A | 1/2000 | Kampner |
| 6,022,509 A | 2/2000 | Matthews et al. |
| 6,042,611 A | 3/2000 | Noiles |
| 6,042,612 A | 3/2000 | Voydeville et al. |
| 6,049,054 A | 4/2000 | Panchison et al. |
| 6,059,833 A | 5/2000 | Doets |
| 6,063,442 A | 5/2000 | Cohen et al. |
| 6,066,176 A | 5/2000 | Oshida |
| 6,087,553 A | 7/2000 | Cohen et al. |
| 6,099,529 A | 8/2000 | Gertzman et al. |
| 6,129,765 A | 10/2000 | Lopez et al. |
| 6,132,469 A | 10/2000 | Schroeder |
| 6,132,674 A | 10/2000 | Compton et al. |
| 6,136,029 A | 10/2000 | Johnson et al. |
| 6,139,574 A | 10/2000 | Vacanti et al. |
| 6,143,036 A | 11/2000 | Comfort |
| 6,143,293 A | 11/2000 | Weiss et al. |
| 6,149,689 A | 11/2000 | Grundei et al. |
| 6,152,962 A | 11/2000 | DeCarlo, Jr. |
| 6,162,257 A | 12/2000 | Gustilo et al. |
| 6,165,222 A | 12/2000 | Hoeppner et al. |
| 6,176,879 B1 | 1/2001 | Reischl et al. |
| 6,187,050 B1 | 2/2001 | Khalili et al. |
| 6,192,272 B1 | 2/2001 | Fiedler et al. |
| 6,193,761 B1 | 2/2001 | Treacy |
| 6,197,065 B1 | 3/2001 | Martin et al. |
| 6,203,844 B1 | 3/2001 | Park |
| 6,206,924 B1 | 3/2001 | Timm |
| 6,217,620 B1 | 4/2001 | Park |
| 6,228,121 B1 | 5/2001 | Khalili |
| 6,231,612 B1 | 5/2001 | Balay et al. |
| 6,240,616 B1 | 6/2001 | Yan |
| 6,253,443 B1 | 7/2001 | Johnson |
| 6,273,891 B1 | 8/2001 | Masini |
| 6,290,726 B1 | 9/2001 | Pope et al. |
| 6,293,971 B1 | 9/2001 | Nelson et al. |
| 6,296,667 B1 | 10/2001 | Johnson et al. |
| 6,302,913 B1 | 10/2001 | Ripamonti et al. |
| 6,306,173 B1 | 10/2001 | Masini |
| 6,309,546 B1 | 10/2001 | Herrmann et al. |
| 6,312,201 B1 * | 11/2001 | Nagaya et al. ................ 409/234 |
| 6,322,728 B1 | 11/2001 | Brodkin et al. |
| 6,340,370 B1 | 1/2002 | Willert et al. |
| 6,352,559 B1 | 3/2002 | Church et al. |
| 6,365,092 B1 | 4/2002 | Backa et al. |
| 6,376,573 B1 | 4/2002 | White et al. |
| 6,383,224 B1 | 5/2002 | Gie et al. |
| 6,391,251 B1 | 5/2002 | Keicher et al. |
| 6,416,553 B1 | 7/2002 | White et al. |
| 6,432,142 B1 | 8/2002 | Kamiya et al. |
| 6,443,991 B1 | 9/2002 | Running |
| 6,447,543 B1 | 9/2002 | Studer et al. |
| 6,447,550 B1 | 9/2002 | Hunter et al. |
| 6,454,811 B1 | 9/2002 | Sherwood et al. |
| 6,458,161 B1 | 10/2002 | Gibbs et al. |
| 6,461,385 B1 | 10/2002 | Gayer et al. |
| 6,475,243 B1 | 11/2002 | Sheldon et al. |
| 6,488,713 B1 * | 12/2002 | Hershberger ............. 623/22.11 |
| 6,497,727 B1 | 12/2002 | Pope et al. |
| 6,506,192 B1 | 1/2003 | Gertzman et al. |
| 6,508,841 B2 | 1/2003 | Martin et al. |
| 6,520,995 B2 | 2/2003 | Church et al. |
| 6,527,774 B2 | 3/2003 | Lieberman |
| 6,527,807 B1 | 3/2003 | O'Neil et al. |
| 6,527,809 B1 | 3/2003 | Doursounian et al. |
| 6,530,958 B1 | 3/2003 | Cima et al. |
| 6,537,321 B1 | 3/2003 | Horber et al. |
| 6,544,472 B1 | 4/2003 | Compton et al. |
| 6,558,428 B2 | 5/2003 | Park |
| 6,572,655 B1 | 6/2003 | Johnson |
| 6,585,772 B2 | 7/2003 | Hunter et al. |
| 6,592,622 B1 | 7/2003 | Ferguson |
| 6,605,293 B1 | 8/2003 | Giordano et al. |
| 6,605,648 B1 | 8/2003 | Johnson et al. |
| 6,610,097 B2 | 8/2003 | Serbousek et al. |
| 6,613,093 B2 | 9/2003 | DeCarlo, Jr. et al. |
| 6,620,200 B1 | 9/2003 | Descamps et al. |
| 6,621,039 B2 | 9/2003 | Wang et al. |
| 6,626,947 B2 | 9/2003 | Lester et al. |
| 6,626,950 B2 | 9/2003 | Brown et al. |
| 6,641,616 B1 | 11/2003 | Grundei et al. |
| 6,645,206 B1 | 11/2003 | Zdeblick et al. |
| 6,652,586 B2 | 11/2003 | Hunter et al. |
| 6,660,040 B2 | 12/2003 | Chan et al. |
| 6,660,224 B2 | 12/2003 | Lefebvre et al. |
| RE38,409 E | 1/2004 | Noiles |
| 6,676,704 B1 | 1/2004 | Pope et al. |
| 6,676,892 B2 | 1/2004 | Das et al. |
| 6,682,566 B2 | 1/2004 | Draenert et al. |
| 6,682,567 B1 | 1/2004 | Schroeder |
| 6,686,437 B2 | 2/2004 | Buchman et al. |
| 6,695,884 B1 | 2/2004 | Townley |
| 6,696,073 B2 | 2/2004 | Boyce et al. |
| 6,709,462 B2 | 3/2004 | Hanssen |
| 6,725,901 B1 | 4/2004 | Kramer et al. |
| 6,726,723 B2 | 4/2004 | Running |
| 6,726,725 B2 | 4/2004 | Hunter et al. |
| 6,740,186 B2 * | 5/2004 | Hawkins et al. ............. 156/242 |
| 6,758,864 B2 | 7/2004 | Storer et al. |
| 6,770,099 B2 | 8/2004 | Andriacchi et al. |
| 6,783,551 B1 | 8/2004 | Metzger et al. |
| 6,800,094 B2 | 10/2004 | Burkinshaw |
| 6,811,569 B1 | 11/2004 | Afriat et al. |
| 6,827,742 B2 | 12/2004 | Hayes, Jr. et al. |
| 6,840,960 B2 | 1/2005 | Bubb |
| 6,866,685 B2 | 3/2005 | Chan et al. |
| 6,869,447 B2 | 3/2005 | Lee et al. |
| 6,896,703 B2 | 5/2005 | Barbieri et al. |
| 6,908,486 B2 | 6/2005 | Lewallen |
| 6,916,342 B2 | 7/2005 | Frederick et al. |
| 6,923,833 B2 | 8/2005 | Wasielewski |
| 6,926,740 B2 | 8/2005 | Lewis et al. |
| 6,945,448 B2 | 9/2005 | Medlin et al. |

| | | |
|---|---|---|
| 6,981,991 B2 | 1/2006 | Ferree |
| 7,141,073 B2 | 11/2006 | May et al. |
| 7,147,819 B2 | 12/2006 | Bram et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,192,448 B2 | 3/2007 | Ferree |
| 7,351,371 B2 | 4/2008 | Nelles et al. |
| 2001/0011190 A1 | 8/2001 | Park |
| 2001/0013166 A1 | 8/2001 | Yan |
| 2001/0030035 A1 | 10/2001 | Oda |
| 2002/0016635 A1 | 2/2002 | Despres et al. |
| 2002/0040245 A1 | 4/2002 | Lester et al. |
| 2002/0062154 A1 | 5/2002 | Ayers |
| 2002/0068980 A1 | 6/2002 | Serbousek et al. |
| 2002/0071827 A1 | 6/2002 | Peterson et al. |
| 2002/0123750 A1 | 9/2002 | Eisermann et al. |
| 2002/0139504 A1 | 10/2002 | Klein |
| 2002/0143403 A1 | 10/2002 | Vaidyanathan et al. |
| 2002/0151983 A1 | 10/2002 | Shetty |
| 2002/0197178 A1 | 12/2002 | Yan |
| 2003/0001282 A1 | 1/2003 | Meynen et al. |
| 2003/0013989 A1 | 1/2003 | Obermiller et al. |
| 2003/0033020 A1 | 2/2003 | Hunter et al. |
| 2003/0049299 A1 | 3/2003 | Malaviya et al. |
| 2003/0050703 A1 | 3/2003 | Harris et al. |
| 2003/0050705 A1 | 3/2003 | Cueille et al. |
| 2003/0069639 A1 | 4/2003 | Sander et al. |
| 2003/0074079 A1* | 4/2003 | McTighe et al. ........... 623/22.42 |
| 2003/0083741 A1 | 5/2003 | Woo et al. |
| 2003/0105529 A1 | 6/2003 | Synder et al. |
| 2003/0111752 A1 | 6/2003 | Wood et al. |
| 2003/0114936 A1 | 6/2003 | Sherwood et al. |
| 2003/0135281 A1 | 7/2003 | Hanssen |
| 2003/0144741 A1 | 7/2003 | King et al. |
| 2003/0144742 A1 | 7/2003 | King et al. |
| 2003/0153981 A1 | 8/2003 | Wang et al. |
| 2003/0153982 A1 | 8/2003 | Pria |
| 2003/0155686 A1 | 8/2003 | Hawkins et al. |
| 2003/0163202 A1 | 8/2003 | Lakin |
| 2003/0171818 A1 | 9/2003 | Lewallen |
| 2003/0200837 A1 | 10/2003 | Matsuura et al. |
| 2003/0220696 A1 | 11/2003 | Levine et al. |
| 2003/0232124 A1 | 12/2003 | Medlin et al. |
| 2003/0236573 A1 | 12/2003 | Evans et al. |
| 2004/0054418 A1 | 3/2004 | McLean et al. |
| 2004/0054421 A1 | 3/2004 | McLean |
| 2004/0064192 A1 | 4/2004 | Bubb |
| 2004/0072010 A1 | 4/2004 | Date et al. |
| 2004/0083004 A1 | 4/2004 | Wasielewski |
| 2004/0088038 A1 | 5/2004 | Dehnad et al. |
| 2004/0098127 A1 | 5/2004 | Charlebois et al. |
| 2004/0102854 A1 | 5/2004 | Zhu |
| 2004/0109853 A1 | 6/2004 | McDaniel |
| 2004/0122521 A1 | 6/2004 | Lee et al. |
| 2004/0126265 A1 | 7/2004 | Takiguchi |
| 2004/0126583 A1 | 7/2004 | Nakamura et al. |
| 2004/0137218 A1 | 7/2004 | Liu et al. |
| 2004/0166340 A1 | 8/2004 | Cairns et al. |
| 2004/0172137 A1 | 9/2004 | Blaylock et al. |
| 2004/0186553 A1 | 9/2004 | Yan |
| 2004/0199258 A1 | 10/2004 | Macara |
| 2004/0199260 A1 | 10/2004 | Pope et al. |
| 2004/0210316 A1 | 10/2004 | King et al. |
| 2004/0225369 A1 | 11/2004 | Lakin et al. |
| 2004/0225371 A1 | 11/2004 | Roger |
| 2004/0229029 A1 | 11/2004 | Bowles et al. |
| 2004/0238410 A1 | 12/2004 | Inoue et al. |
| 2004/0243133 A1 | 12/2004 | Materna |
| 2005/0004677 A1 | 1/2005 | Johnson |
| 2005/0004678 A1 | 1/2005 | Richards |
| 2005/0004680 A1 | 1/2005 | Saladino et al. |
| 2005/0010303 A1 | 1/2005 | Nogier |
| 2005/0025656 A1 | 2/2005 | Bhaduri et al. |
| 2005/0031704 A1 | 2/2005 | Ahn |
| 2005/0032025 A1 | 2/2005 | Bhaduri et al. |
| 2005/0033298 A1* | 2/2005 | Hawkes et al. ................. 606/61 |
| 2005/0035052 A1 | 2/2005 | Kelly et al. |
| 2005/0048193 A1 | 3/2005 | Li et al. |
| 2005/0049713 A1 | 3/2005 | Garber et al. |
| 2005/0060040 A1 | 3/2005 | Auxepaules et al. |
| 2005/0065307 A1 | 3/2005 | King et al. |
| 2005/0065604 A1 | 3/2005 | Stoll |
| 2005/0071015 A1 | 3/2005 | Sekel |
| 2005/0085820 A1 | 4/2005 | Collins et al. |
| 2005/0085915 A1 | 4/2005 | Steinberg |
| 2005/0087915 A1 | 4/2005 | Pope et al. |
| 2005/0090905 A1 | 4/2005 | Hawkins et al. |
| 2005/0100470 A1 | 5/2005 | Lefebvre et al. |
| 2005/0107883 A1 | 5/2005 | Goodfried et al. |
| 2005/0149199 A1 | 7/2005 | Steinberg |
| 2005/0171614 A1 | 8/2005 | Bacon |
| 2005/0184134 A1 | 8/2005 | Charlebois et al. |
| 2005/0234559 A1 | 10/2005 | Fernandez et al. |
| 2005/0242162 A1 | 11/2005 | Medlin et al. |
| 2005/0246032 A1 | 11/2005 | Bokros et al. |
| 2006/0002810 A1 | 1/2006 | Grohowski, Jr. |
| 2006/0003179 A1 | 1/2006 | Wang et al. |
| 2006/0018942 A1 | 1/2006 | Rowe et al. |
| 2006/0241776 A1 | 10/2006 | Brown et al. |
| 2006/0241781 A1 | 10/2006 | Brown et al. |
| 2007/0021838 A1 | 1/2007 | Dugas et al. |
| 2007/0129809 A1 | 6/2007 | Meridew et al. |
| 2007/0150068 A1 | 6/2007 | Dong et al. |
| 2007/0173948 A1 | 7/2007 | Meridew et al. |
| 2007/0196230 A1 | 8/2007 | Hamman et al. |
| 2007/0243312 A1 | 10/2007 | Bulko |
| 2007/0250175 A1 | 10/2007 | Meridew et al. |
| 2007/0264152 A1 | 11/2007 | Zhao |
| 2009/0084491 A1 | 4/2009 | Uthgenannt et al. |

FOREIGN PATENT DOCUMENTS

| | | |
|---|---|---|
| DE | 3130732 | 5/1983 |
| DE | 3205526 | 9/1983 |
| DE | 8612735 | 3/1989 |
| DE | 41 33 433 | 5/1993 |
| DE | 19726961 | 11/1998 |
| EP | 0214885 | 3/1987 |
| EP | 0378928 | 7/1990 |
| EP | 0538987 | 4/1993 |
| EP | 0551794 | 7/1993 |
| EP | 0577179 | 1/1994 |
| EP | 0612509 | 8/1994 |
| EP | 0648478 | 4/1995 |
| EP | 0 807 426 | 11/1997 |
| EP | 0806921 | 11/1997 |
| EP | 0985386 | 3/2000 |
| EP | 1082949 | 3/2001 |
| EP | 1 236 450 | 9/2002 |
| EP | 1312323 | 5/2003 |
| EP | 1 384 456 | 1/2004 |
| EP | 1421918 | 5/2004 |
| EP | 1430856 | 6/2004 |
| FR | 2 148 322 | 3/1973 |
| FR | 2775586 | 9/1999 |
| FR | 2803740 | 7/2001 |
| GB | 2001247 | 1/1979 |
| WO | WO-92/18069 | 10/1992 |
| WO | WO-96/13233 | 5/1996 |
| WO | WO-96/23459 | 8/1996 |
| WO | WO-00/38598 | 7/2000 |
| WO | WO-01/70141 | 9/2001 |
| WO | WO-02/07652 | 1/2002 |
| WO | WO-2004069107 | 8/2004 |
| WO | WO-2004/080340 | 9/2004 |
| WO | WO-2006007861 | 1/2006 |

OTHER PUBLICATIONS

Bram, Martih et al., High-Porosity Titanium, Stainless Steel, and Superalloy Parts, Advanced Engineering Matertals 2000, 2, No. 4, 196-199.

International Search Report and Written Opinion for PCT/US2007/03811 mailed Sep. 27, 2007.

Michael S. Bradford, M.D. and Wayhe G. Paprosky, M.D., F.A.C.S., Total Accetabular Transplant Allograft Reconstruction of the Severely Deficient Acetabulum, Sunrise Hospital and Medical Center, Las Vegas, NV and Rush-Presbyterian-St. Lukes Medical Center, Chicago, IL, 1995 by W.B. Saunders Company, pp. 1-15.

Oliveira, M.V., et al., Porous Structure Characterization in Titanium Coating for Surgical Implants, © 2002, Materials Research, vol. 5, No. 3, 269-273.

Wen, C.E., et al., Novel titanium foam for bone tissue engineering, J. Mater. Res., vol. 17, No. 10, Oct. 2002, 2633-2639.

Wen, C.E., et al., Processing and mechanical properties of autogenous titanium implant materials, Journal of Materials Science: Materials in Medicine 13 (2002), 397-401.

Wen, C.E.. Processing of biocompatible porous Ti and Mg, Scripta Materialia 45 (2001) 1147-1153.

Wheeler, K.R., et al., Porous Metals as a Hard Tissue Substitute. Part II. Porous Metal Properties, Biomat., Med. Dev., Art. Org., 1(2), 337-348 (1973).

International Search Report and Written Opinion for PCT/US2008/002372 mailed Dec. 9, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

International Search Report and Written Opinion for PCT/US2008/002372 mailed Jul. 30, 2008 claiming benefit of U.S. Appl. No. 11/709,549, which claims benefit of U.S. Appl. No. 11/546,500, which claims benefit of U.S. Appl. No. 11/357,868, which claims benefit of U.S. Appl. No. 11/294,692, which claims benefit of U.S. Appl. No. 11/111,123.

Laptev, A. et al. "Study of Production Route for Titanium Parts Combining Very High Porosity and Complex Shape" Powder Metallurgy, vol. 47, No. 1 (2004), pp. 85-92.

* cited by examiner

METHOD AND APPARATUS FOR USE OF POROUS IMPLANTS

CROSS-REFERENCE TO RELATED APPLICATIONS

This application is a continuation-in-part of U.S. patent application Ser. No. 11/294,692 filed Dec. 5, 2005, which is a continuation-in-part of U.S. patent application Ser. No. 11/111,123 filed on Apr. 21, 2005.

This application is related to U.S. patent application Ser. No. 11/357,868 filed Feb. 17, 2006.

This application is related to U.S. patent application Ser. No. 11/546,500 filed Oct. 11, 2006.

This application is related to U.S. patent application Ser. No. 11/709,549 filed Feb. 22, 2007.

The disclosures of the above applications are incorporated herein by reference.

INTRODUCTION

Porous coated implants have been used to promote biologic fixation of surrounding bony tissue. In one example, porous material may be coated on an exterior surface of a prosthetic implant to encourage ingrowth of surrounding bone into the pore spaces of the porous material. Typically, the porous coating may comprise stainless steel, titanium, titanium alloys, tantalum, cobalt-chromium alloys, ceramics, polymers and other materials that are suited for use in a biocompatible environment. Various joining methods have been employed to attach the porous coating to a desired prosthetic implant. For example, soldering, brazing, adhesive joining, laser welding, diffusion bonding, metallurgic bonds and mechanical joining have been shown to suitably attach the porous material to a desired implant.

SUMMARY

The present teachings provide an orthopedic implant. The implant includes a metal portion having an internal three-dimensional cavity, the cavity having an opening to an outer surface of the metal portion, a ledge circumferentially surrounding at least a portion of the opening, and a porous metal insert formed in a three-dimensional shape conforming to the shape of the cavity and enclosed by the cavity without being bonded to the cavity. The insert is retained inside the cavity by the ledge.

The present teachings provide a method for attaching a porous metal insert to a substrate. The method includes forming a three-dimensional cavity in the substrate, the cavity having a first dimension along a first axis, the cavity defining an opening to an outer surface of the substrate, the opening having a second dimension along the first axis, the first dimension greater than the second dimension. The method further includes forming a porous metal insert having a three-dimensional shape mateable with the cavity and a third dimension along the first axis greater than the second dimension, cooling the insert below ambient temperature until the third dimension is equal or smaller than the second dimension, inserting the insert through the opening, and retaining the insert in the cavity by the ledge upon return to ambient temperature.

In another aspect, the method includes cooling a three-dimensional porous metal insert below ambient temperature, reducing at least a first dimension of the insert, and inserting the cooled metal insert through an opening into a three-dimensional cavity of a metal substrate, the opening having a second dimension parallel to the first dimension of the insert. The method further includes returning the metal insert to ambient temperature, returning the first dimension to a length greater than the second dimension, and retaining the metal insert in the cavity of the substrate.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings are illustrated for particular applications, the present teachings can be used for any orthopedic procedures in which porous inserts are used. Moreover, while variously metal inserts are illustrated, the inserts and theirs applications are merely exemplary.

Referring to FIGS. 1A-1E, various exemplary porous metal inserts or augments 100 according to the present teachings are illustrated. In general, the porous metal inserts illustrated in FIGS. 1A-1C comprise a uniform porous metal material or block 102. The porous metal insert 100 of FIG. 1A has a semi-circular shape. The porous metal insert 100 of FIG. 1B includes an integral retaining structure in the form of tapered sidewalls. The porous metal insert 100 of FIG. 1C includes apertures 104 formed therethrough. The apertures 104 may be used for attachment purposes for securing the insert 100 at a desired location, or for securing items to the insert 100.

Figure 1A:
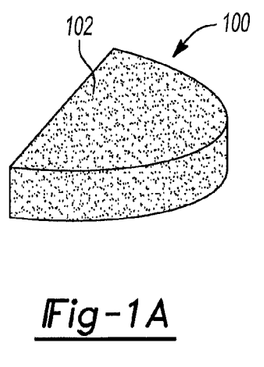
FIG. 1A is a perspective view of an exemplary porous insert according to the present teachings.
Figure 1B:
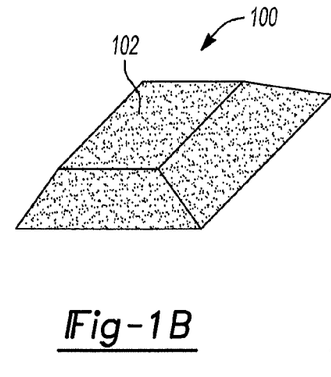
FIG. 1B is a perspective view of an exemplary porous insert according to the present teachings.
Figure 1C:
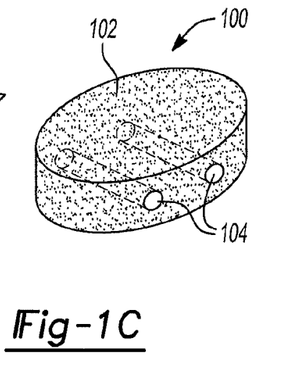
FIG. 1C is a perspective view of an exemplary porous insert according to the present teachings.
Figure 1D:
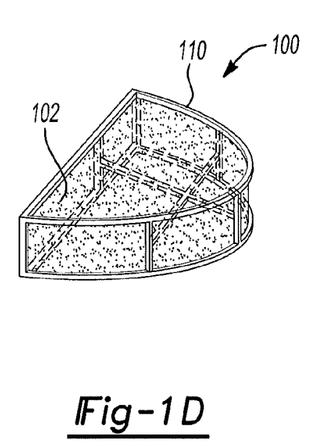
FIG. 1D is a perspective view of an exemplary porous insert incorporating a metal framework according to the present teachings.
Figure 1E:
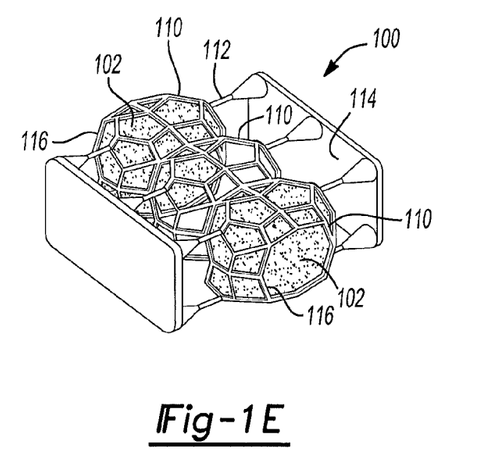
FIG. 1E is a perspective view of a pair of exemplary porous inserts each having a metal framework and shown interconnected through a carrier in a manufacturing process according to the present teachings.

The porous metal inserts illustrated in FIGS. 1D and 1E comprise a uniform porous metal block 102 captured within a solid metal framework 110. The framework 110 is adapted to provide additional strength to the insert 100. The framework 110 can be arranged exclusively on an outboard surface of the porous metal block 102, exclusively within the porous metal block 102 or as a combination. The insert 100 illustrated in FIG. 1E includes a series of interconnected frameworks 110, posts 112 and a carrier 114 constructed in a preliminary manufacturing step. The framework 110 may additionally or alternatively comprise wall surfaces.

The porous metal inserts 100 shown in FIGS. 1A-1E can be employed in cooperation with an implantable prosthesis and provide a suitable surface area for encouraging ingrowth of natural bone and/or soft tissue. In addition, the porous metal inserts 100 may be adapted to provide mechanical strength in a load-bearing application, or simply be employed as filler in cooperation with various prosthesis components. In this way, the porous metal inserts 100 can be load-bearing in applications having compression, tension, cantilever, static or dynamic loads. In other aspects, the porous metal inserts 100 can be used as an anchoring devices to facilitate bone fixation or healing in which the bone may be subjected to compression, tension or other loads. Additional porous metal inserts having various structures and features and various exemplary applications are described in co-pending and commonly assigned patent application Ser. No. 11/294,692, filed on Dec. 5, 2005, and Ser. No. 11/111,123 filed on Apr. 21, 2005, the disclosures of which are incorporated by reference herein.

According to the present teachings, the porous metal used in the inserts 100 can include stainless steel, titanium, titanium alloys, cobalt-chromium alloys and other materials that are suited for use in a biocompatible environment such as disposed on an implantable bone prosthesis, including Regenerex™, a porous titanium construct manufactured from Ti-6Al-4V alloy and commercially available from Biomet, Inc., of Warsaw, Ind. A method for making a porous metal implant is disclosed in co-pending and commonly assigned patent application Ser. No. 11/357,929, filed Feb. 17, 2006, the disclosure of which is incorporated by reference herein.

In one method of making the porous metal, a sponge material can be utilized as a template. The sponge material may be naturally occurring sponge, such as sponge found in the ocean, or alternatively, an artificial sponge, such as a synthetic polymer sponge. The sponge material can then be coated or saturated with fine metal particles. Next, the sponge material coated with the fine metal particles can be subjected to heat. Exposure to heat causes the sponge to melt away leaving the porous metal block 102. At this point, the porous metal block may be implanted as is, or placed within a solid metal framework (such as framework 110 shown in FIGS. 1D and 1E). It is appreciated that the framework 104 may be arranged around the sponge material prior to the melting away of the sponge. Likewise, the sponge material may provide a uniform or non-uniform pattern.

In another aspect, anti-infective agents (i.e. antibiotics), osteoconductive agents (i.e., hydroxyapatite), autologous blood products activated by thrombin to induce clots (i.e., blood, platelet rich plasma, autologous stem cells derived from any location within the body), hydrogels, either alone or containing autologous or allogenic cells, peptides, or other biologically active ingredients that induce or aide bone formation (i.e., bone morphogenic proteins) may be added and/or infiltrated to the porous metal of the implants, inserts, anchors and/or bone screws disclosed herein. Further, the porous metal structures described herein may also act as a carrier for bulk allograft or demineralized bone matrix products. Other growth promoters can be added and/or infiltered to the porous material of the implants, inserts, anchors and bone screws described herein to promote appropriate soft or hard tissue response, ingrowth or attachment.

According to another method of making the inserts 100, a laser can be utilized to contour a block of suitable material into a desired shape. As discussed above, a suitable material may comprise stainless steel, titanium, titanium alloys, cobalt-chromium alloys and other materials that are suited for use in a biocompatible environment such as disposed on an implantable bone prosthesis. In one implementation, a computer can be used to design the desired geometry and properties of the insert. In one method, a bone scan may be performed to create a mathematical model. Another method is by way of computer aided design software. Once the model has been created in the computer, the computer can communicate with the laser to remove or melt away portions of material in the block to reproduce the computer model. In one implementation, this process may be used to create the framework 110. A subsequent step requires the porous material 102 to be placed within the framework 110. In another implementation, this process may be used to create the framework 110 and the porous material 102 simultaneously. In such a method, the laser would be utilized to melt identified portions of material to a desired consistency which, when solidified would provide the porous material 102.

In another method of making the inserts 100, sections or layers of material are cut out of sheets of metal and stacked. The stacked layers can be subsequently joined by a joining process such as by welding, sintering or diffusion bonding. During a welding operation, the framework and the porous material 102 may be oppositely charged, by which a uniform melt may occur between touching surfaces. The material utilized is similar with those mentioned above. The sheets may be cut by any suitable method such as by laser, machined or other process. It is appreciated that this method may be used to create a framework, such as framework 110. A subsequent assembly step may require the porous material 102 to be placed within the framework 110. It is contemplated, however, that the framework 110 and the porous material 102 may be defined concurrently during the creation of each layer.

With reference now to FIG. 1E, the insert 100 can include a series of interconnected frameworks 110, posts 112, and a carrier 114 constructed in a preliminary step. The carrier 114 and posts 112 are used to create a casting. The porous material 102 is then located into the outer frameworks 110 through outer passages 116 defined by the frameworks 102. The intermediate framework 110 (without the porous material 102) along with the carrier 114 and posts 112 are subsequently removed leaving a pair of standalone frameworks 110 having porous material 102 contained therein. Alternatively, the intermediate framework 110 may comprise porous material therein. In another example, the collective series of frameworks 110 can be removed from the carrier 114 and posts 112 and subsequently left as a unitary component rather than being disconnected from each other.

In one exemplary method, the porous material 102 is located within the frameworks 110 as a secondary step. In this implementation, the temperature of the frameworks 110 is raised to a temperature that is below the melting point of the frameworks but enough to cause the frameworks 110 to expand. Additionally or alternatively, the temperature of the porous material 102 is reduced to cause the porous material 102 to contract. Once the desired geometries have been obtained, the porous material 102 is passed through the passages 116 on the frameworks 110. Once the frameworks 110 and the porous material 102 returns to ambient temperature, the porous material 102 has too large of an outer dimension to pass through the passage 116 of the frameworks 110. As a result, the porous material 102 is captured within the frameworks 110.

In another exemplary method, the porous material 102 and the frameworks 110 are initially at ambient temperature. The porous material 102 is then press-fit through the passages 116 of the frameworks 110. Next, the entire assembly of the insert 100 is heated to a temperature that causes the contact surfaces of the porous material 102 and frameworks 110 to weld together. Once the assembly of the insert 100 returns to ambient temperature, the porous material 102 remains secured to the frameworks 110.

Referring to FIGS. 2-5, of method of attaching a porous metal augment or insert 100 to a substrate 200 according to the present teachings is illustrated. In one exemplary application, the porous metal insert 100 can be made of porous titanium and the substrate 200 can be made of nonporous or solid metal such as CoCrMo, although the present teachings are not limited to these materials, as discussed above. For example, the substrate 200 can also be a porous metal of different material than the insert 100. In another aspect, a coralline or other porous ceramic material can be used for the substrate 200.

The method illustrated in FIGS. 2-5 uses a mechanical junction for attaching the insert 100 to the substrate 200 instead of the alternative methods that use adhesive fixation, interposition of a tertiary material, or direct bonding via heating. In this respect, the use of adhesives can clog the pores of the porous insert 100 and also create additional surface interactions. The use of a tertiary material layer can result in an increase of the thickness of the assembly, or a decrease in the thicknesses of the desired materials, and/or also create unnecessary additional surface interactions. The use of direct bonding of porous metal to a solid substrate requires sufficient heating of the substrate, resulting in a decrease in desired mechanical properties of the substrate 200.

Figure 2:
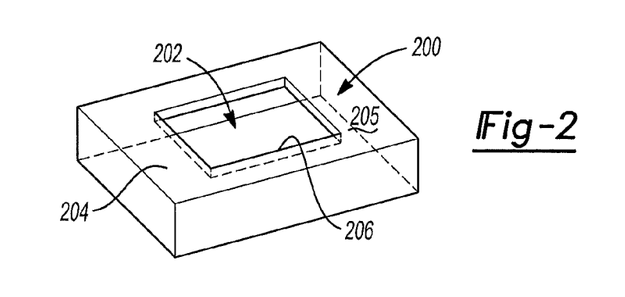
FIG. 2 is a perspective view of an exemplary substrate prepared for receiving a porous insert according to the present teachings.
Figure 3:
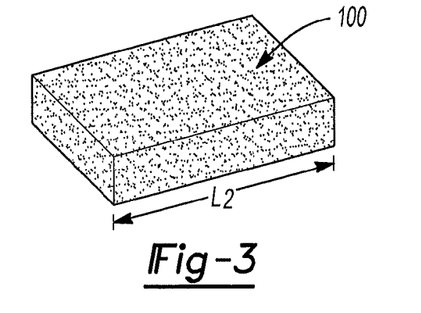
FIG. 3 is a perspective view of an exemplary insert for attachment to the substrate of FIG. 2.
Figure 5:
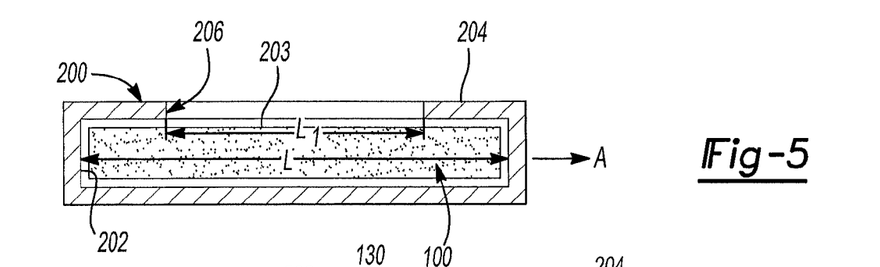
FIG. 5 is a sectional view of FIG. 4 taken along axis 5-5.

The mechanical junction method traps the porous metal insert 100 in an internal cavity or pocket 202 of the solid substrate 200. Specifically, a three-dimensional cavity 202 can be machined or cast into the solid substrate 200, as shown in FIG. 2. The cavity 202 can be in the form of a blind bore or trough and can be bounded on all sides by the substrate 200, except for an area in the form of an opening 206 communicating with an outer surface 205 of the substrate. In other aspects, the cavity 202 may communicate with an outer surface of the substrate 200 by more than one openings, such as two opposite openings for a through bore, or other openings. The opening 206 can be circumferentially completely or partially surrounded by a retaining ledge 204 of the substrate 200. The opening 206 can have a dimension L1 bounded by the ledge 204 with L1 being smaller than a corresponding dimension L of the cavity 202 along a direction A, as shown in FIG. 5. The cavity 202 can have a three-dimensional shape complementary to the shape of the porous metal insert 100. The mating porous metal insert 100, however, can be slightly too oversized to be received through the opening 206 of the cavity 202 at ambient temperature.

Figure 4:
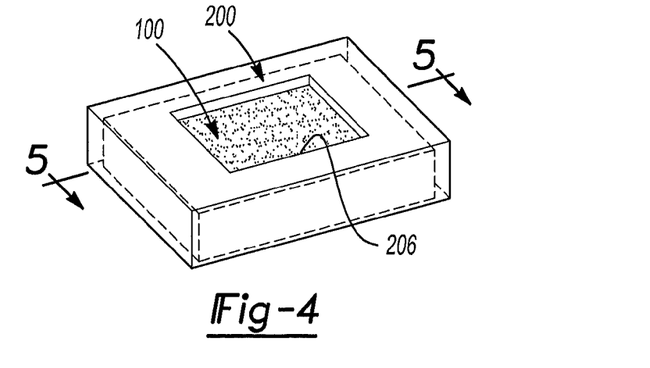
FIG. 4 is a perspective view of the insert of FIG. 3 shown attached to the substrate of FIG. 2.

For example, the porous metal insert 100 can have a dimension L2 greater than the corresponding dimension L1 of the opening 206 along the same direction A. The dimension L2 can be approximately equal to the dimension L of the cavity 202, such that the porous metal insert 100 can fit snugly into the cavity 202, although some play may be optionally provided for by making L2 slightly smaller than L. The porous metal insert 100 can be rapidly cooled below ambient temperature to induce the material of the porous metal insert 100 to shrink sufficiently for insertion into the cavity 202 through the opening 206. For example, the porous metal insert 100 can be cooled with liquid nitrogen. Once cooled, the porous metal insert 100 can be pressed into the cavity 202 through the opening 206 of the solid substrate 200. Upon return to ambient temperature, the porous metal material of the insert 100 expands to return to its original size, and the porous metal insert 100 is thereby trapped in the cavity 202 by the retaining ledge 204, as shown in FIGS. 4 and 5.

Figure 5A:
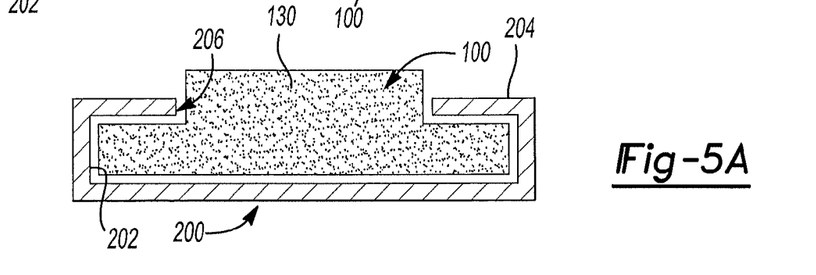
FIG. 5A is a sectional view of a porous insert in a metal substrate according to the present teachings.

The ledge 204 can extend over and overlap with a portion of a surface 203 the porous metal insert 100 adjacent to the opening 206 preventing the porous metal insert 100 from sliding out of the opening 206. Further, the ledge 204 can extend only over portion of the perimeter of the porous metal insert 100. In the example illustrated in FIGS. 1-5, the ledge 204 can be formed only along two opposite sides or along all four sides, or over portions of those sides. It will be appreciated that the ledge 204 can have different shapes, sizes and extents, which can be selected according to manufacturing and other considerations, including the ability and ease in retaining the porous metal insert 100. The ledge 204 can be, for example, straight, as shown in FIG. 5, or L-shaped, or angled or curved toward the interior of the cavity 202, or other shapes. In another aspect, and referring to FIG. 5A, a portion 130 of the insert 100 can extend outside the opening 206 and outside the cavity 202, thereby providing a porous metal surface for tissue contact.

Optionally, the solid substrate 200 can also be heated below a critical temperature that does not alter the material properties of the substrate, to cause the substrate 200 to expand, thereby further facilitating insertion of the porous metal insert 100 into the cavity 202. Alternatively, other non thermal methods of changing the dimensions and shape of the substrate 20 and/or insert 100 can be used to allow for assembly of the insert in the substrate. For example, methods of changing kinetic energy can be used. Spinning the substrate 200 at a sufficiently high rate of revolution can cause expansion of the dimensions of the substrate 200 to allow the insert 100 to be received in the cavity 202. As the spinning is reduced and stopped, the substrate 200 shrinks in size, and can cold weld with the insert 100.

Figure 6:
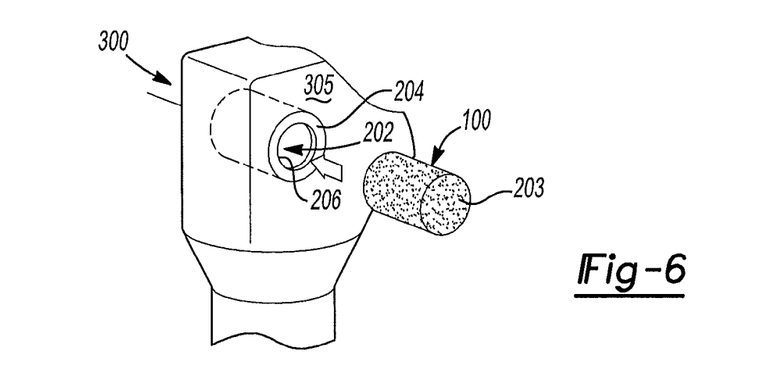
FIG. 6 is a perspective view of a porous insert being implanted into a femoral implant according to the present teachings.

Referring to FIG. 6, a method of utilizing a porous metal insert 100 with a bone implant 300 as the substrate is illustrated. The exemplary bone implant 300 shown is a portion of a femoral hip stem. It is appreciated that while the exemplary bone implant 300 is shown as a femoral hip stem, other prosthesis components may similarly be employed. A cylindrical cavity 202 can be manufactured in the prosthesis 300, for example by machining or casting, or other methods. The cavity 202 has an opening 206 to the outer surface 305 of the implant 300. The opening 206 can be partially or fully circumferentially surrounded by a ledge 206. As described above, the porous metal insert 100, which is slightly oversized, is first rapidly cooled so that it can be inserted into the cavity 202 through the opening 206. After insertion, the porous metal insert 100 is allowed to reach ambient temperature. The ledge 204 can overlap a portion of the surface 203 of the porous metal insert 100 adjacent to the opening 206, thereby trapping the porous metal insert 100 into the cavity 202. As discussed above, the exemplary Regenerex™ material possesses an average porosity of about 67 percent, which can corresponds to a greater linear shrinkage of relative to a comparable solid metal material of the substrate 200. For example, immersing the porous metal insert 100 in liquid nitrogen can reduce a linear dimension L2 of about 0.5 inches by about 0.001-0.002 inches, or by about 4-8%.

It will be appreciated that the porous metal insert 100 and the cavity 202 formed in the substrate can have various three-dimensional shapes, including cylindrical, prismatic, parallelepiped, cubical, spherical, ovoid, or other shapes.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for attaching a metal insert to a substrate, the method comprising:
   providing a substrate that comprises an implantable orthopedic component of nonporous metal;
   forming a three-dimensional cavity defined by inner walls of the substrate, the cavity having a first dimension along a first axis, the cavity defining an opening to an outer surface of the substrate, the opening at least partially bounded by a ledge and having a second dimension along the first axis, the first dimension greater than the second dimension wherein the inner walls include side walls and a closed end wall, the closed end wall having a surface that faces the opening;
   forming a porous metal insert having a three-dimensional shape mateable with the cavity and a third dimension along the first axis greater than the second dimension, the porous metal insert having a porous metal outer surface configured to encourage ingrowth of soft tissue;
   cooling the insert below ambient temperature until the third dimension is equal or smaller than the second dimension;
   inserting the insert through the opening; and
   retaining the insert in the cavity by the ledge upon return to ambient temperature wherein the porous metal outer surface of the porous metal insert engages at least the closed end wall of the inner walls of the substrate.

2. The method of claim 1, wherein the cavity and the insert are cylindrical.

3. The method of claim 1, wherein the cavity and the insert are prismatic.

4. The method of claim 1, wherein forming the cavity further comprises machining the cavity into the substrate.

5. The method of claim 1, wherein forming the cavity further comprises casting the cavity into the substrate.

6. The method of claim 1, wherein the ledge circumscribes the entire opening.

7. The method of claim 1, wherein the cavity is a blind bore.

8. The method of claim 1 wherein the porous metal insert is formed entirely of porous material.

9. The method of claim 1 wherein the porous metal insert is uniformly porous.

10. The method of claim 9 wherein an entirety of the porous metal insert is retained within the cavity.

11. A method for attaching a porous metal insert to a metal substrate, the method comprising:
    providing a metal substrate that is a solid metal portion of an orthopedic implant;
    cooling a three-dimensional porous metal insert below ambient temperature, the porous metal insert having a porous metal outer surface configured to encourage ingrowth of soft tissue;
    reducing at least a first dimension of the insert;
    inserting the cooled metal insert through an opening into a three-dimensional cavity defined by inner walls of the metal substrate, the opening having a second dimension parallel to the first dimension of the insert wherein the inner walls include side walls and a closed end wall, the closed end wall having a surface that faces the opening;
    returning the metal insert to ambient temperature;
    returning the first dimension to a length greater than the second dimension; and
    retaining the metal insert in the cavity of the substrate wherein the porous metal outer surface of the porous metal insert engages at least the closed end wall of the inner walls of the metal substrate.

12. The method of claim 11, further comprising machining the cavity into the substrate.

13. The method of claim 11, further comprising casting the cavity into the substrate.

14. The method of claim 11, wherein cooling the insert further comprises immersing the insert in liquid nitrogen.

15. The method of claim 11, wherein cooling the insert comprises reducing a linear dimension of the insert by about 4-8%.

16. The method of claim 11, further comprising heating the substrate.

17. The method of claim 11 wherein the porous metal insert is uniformly porous.

18. The method of claim 11 wherein the porous metal insert is formed entirely of porous material.

19. The method of claim 18 wherein an entirety of the porous metal insert is retained within the cavity.

20. A method for attaching a metal insert to a substrate, the method comprising:
    providing an orthopedic implant that comprises a substrate formed of nonporous metal;
    forming an opening in the substrate, the opening having a first outer dimension along a first axis;
    forming a cavity defined by inner walls of the substrate, the cavity having a second outer dimension along the first axis, the second outer dimension being greater than the first outer dimension, wherein a retaining ledge is formed on the substrate at a transition between the opening and the cavity wherein the inner walls include side walls and a closed end wall, the closed end wall having a surface that faces the opening;
    forming a porous metal insert made entirely of porous metal material configured to encourage ingrowth of soft tissue and having a three-dimensional shape mateable with the cavity and a third outer dimension along the first axis greater than the first outer dimension;
    cooling the insert below ambient temperature until the third outer dimension is equal or smaller than the first outer dimension;
    inserting the insert through the opening; and
    retaining the insert in the cavity by the retaining ledge upon return to ambient temperature wherein the porous metal insert engages at least the closed end wall of the inner walls of the substrate.

21. The method of claim 20 wherein the cavity and the insert are cylindrical.

22. The method of claim 20 wherein the cavity and the insert are prismatic.

23. The method of claim 20 wherein forming the cavity further comprises machining the cavity into the substrate.

24. The method of claim 20 wherein forming the opening and the cavity further comprises casting the opening and the cavity into the substrate.

25. The method of claim 20 wherein the ledge circumscribes the entire opening.

26. The method of claim 20 wherein the cavity is a blind bore.

27. The method of claim 20 wherein providing the substrate comprises providing a femoral hip stem.

28. The method of claim 20 wherein retaining the insert in the cavity comprises positioning a portion of the insert at a location that protrudes outside of the opening and beyond the retaining ledge.

29. The method of claim 20, further comprising heating the substrate.

30. The method of claim 20 wherein an entirety of the porous metal insert is retained within the cavity.

* * * * *